US012751789B2

(12) United States Patent
Sancho et al.

(10) Patent No.: US 12,751,789 B2
(45) Date of Patent: Oct. 6, 2026

(54) SYSTEMS AND METHODS FOR GAP DETECTION DURING ABLATION

(71) Applicant: Ablaview, S.L., Madrid (ES)

(72) Inventors: Juan Sancho, Madrid (ES); David Herranz, Alpedrete (ES); Christophe Bailleul, Paris (FR); James Greene, Shelfield Green (GB)

(73) Assignee: Ablaview, S.L., Madrid (ES)

( * ) Notice: Subject to any disclaimer, the term of this patent is extended or adjusted under 35 U.S.C. 154(b) by 326 days.

(21) Appl. No.: 18/205,951

(22) Filed: Jun. 5, 2023

(65) Prior Publication Data

US 2023/0404696 A1 Dec. 21, 2023

(30) Foreign Application Priority Data

Jun. 9, 2022 (EP) .................................... 22382554

(51) Int. Cl.
*A61B 18/14* (2006.01)
*A61B 90/00* (2016.01)

(52) U.S. Cl.
CPC .......... *A61B 90/06* (2016.02); *A61B 18/1492* (2013.01); *A61B 2090/061* (2016.02)

(58) Field of Classification Search
CPC ...... A61B 18/1492; A61B 2018/00577; A61B 2018/00636; A61B 2018/00642; A61B 2018/00982; A61B 5/0066; A61B 5/0084; A61B 5/0036
See application file for complete search history.

(56) References Cited

U.S. PATENT DOCUMENTS

2013/0204134 A1 8/2013 Harks et al.
2015/0119872 A1* 4/2015 Govari ................ A61B 5/0084 606/34
2016/0235303 A1 8/2016 Fleming et al.
2017/0027639 A1* 2/2017 Margallo Balbás . A61B 5/6852
2018/0125575 A1* 5/2018 Schwartz ........... A61B 18/1492
2021/0085287 A1* 3/2021 Hennersperger ......... A61B 8/12
2021/0212755 A1 7/2021 Jimenez et al.

* cited by examiner

*Primary Examiner* — Beverly M Flanagan
*Assistant Examiner* — Abigail M Ziegler
(74) *Attorney, Agent, or Firm* — Sterne, Kessler, Goldstein & Fox P.L.L.C.

(57) ABSTRACT

Described herein are systems, methods for detecting gaps between lesions formed in tissue during ablation. A system includes a catheter that has proximal section, a distal section, and a shaft coupled between the proximal section and the distal section. A plurality of optical fibers are located within the catheter and are coupled to a computing device. The computing device includes a memory and a processor configured to receive, from the optical fibers, optical measurement data of a portion of tissue during or after an ablation, identify one or more optical properties of the portion of tissue by analyzing the optical measurement data, and detect a presence or an absence of a gap between one or more lesions formed in the portion of tissue based on the one or more optical properties.

15 Claims, 11 Drawing Sheets

300

SYSTEMS AND METHODS FOR GAP DETECTION DURING ABLATION

CROSS-REFERENCE TO RELATED APPLICATIONS

This application claims priority to EP Appl. No. 22382554.8 filed on Jun. 9, 2022, the disclosure of which is incorporated by reference herein in its entirety.

BACKGROUND

Field

Embodiments of the present disclosure relate to systems, methods, and devices for detecting gaps between lesions formed in tissue during ablation by a catheter.

Background

Ablation is a medical technique for producing tissue necrosis. It is used to help treat different pathologies including cancer, Barret's esophagus, or cardiac arrhythmias, among others. Atrial fibrillation (AF) is a common type of cardiac arrhythmia with an estimated 33.5 million people worldwide suffering from this condition in 2010. AF increases the risk of stroke by a factor 5 and is a leading healthcare problem in the developed world. Commonly used, available drug therapies to control heart rhythm in AF patients may have significant shortcomings in terms of effectiveness and may cause serious side effects, resulting in reduced quality of life for patients.

Cardiac catheter ablation therapy may be a minimally invasive procedure that employs a thin, steerable therapeutic catheter that uses energy to create lesions in cardiac tissue to treat cardiac rhythm abnormalities, including atrial fibrillation (AF). Therapy success depends on the clinician's ability to ablate tissue fully through the heart wall and without missing any gaps between ablation points that can be opportunities for AF recurrence. Currently, clinicians cannot determine the quality of catheter contact, contract stability, energy delivered, or quality of ablations performed in real-time.

In some cases, various energy sources may be utilized for ablation, including cryogenic cooling for cryoablation, radiofrequency (RF) ablation, using pulsed electric fields for electroporation ablation, microwave, laser, photoacoustic/ultrasound, and the like. Traditional RF cardiac ablation may result in significant complications associated with perforations or unintended thermal damage to adjacent structures, as such ablation uses thermal means to create the lesion. To that extent, pulsed field ablation (PFA) uses electromagnetic pulses to generate non-thermal lesions during the ablation process. PFA may use electrodes to cause irreversible electroporation of the cells within it, ultimately leading to cell death. Although this technique reduces complications associated to thermal damage, only a limited or minimal necrosis due to thermal damage might be present in the tissue at the surface of the electrode. Current technologies are limited in showing the clinician whether the lesion created by the PFA energy at the selected parameters will result in irreversible electroporation and a subsequent permanent lesion. Lack of such information may lead to significant levels of recurrence of cardiac arrythmias. Having the capability to directly assess lesion creation through use of photonics, would enable to clinicians to create safer, more durable and continuous lesions to treat AF and reduce its recurrence due to creating which are non-transmural or gaps in area of treatment.

BRIEF SUMMARY

Accordingly, there may be a need for providing new methods, devices, and systems for a real-time or near real-time visualization for detecting gaps between lesions formed in tissue during tissue ablation. In embodiments presented herein, optical systems, consoles or processing devices, and catheters may provide optical measurements for understanding optical properties, such as tissue anisotropy and birefringence of tissue, in order to detect the absence or presence of one or more gaps in lesions formed in tissue during ablation. By optically monitoring tissue and analyzing the optical properties for birefringence, systems, methods, and devices described herein may identify gaps in the ablation line during ablation procedures in order to significantly reduce the rate of recurrence of arrhythmias and improve the success rate of ablations.

In an embodiment, an example method is described. The method includes positioning a catheter in a portion of tissue during or after an ablation. The catheter includes a proximal section, a distal section comprising a plurality of optical ports, and a shaft coupled between the proximal section and the distal section, in which at least one optical port is in contact with the portion of tissue. The method further includes acquiring optical measurement data using the at least one optical port in the catheter while moving the distal section of the catheter along an ablation line in the portion of tissue, identifying one or more optical properties of the portion of tissue by analyzing the optical measurement data using a computing device coupled to the catheter, and detecting a presence or an absence of a gap between one or more lesions formed in the ablation line in the portion of tissue based on the one or more optical properties.

In another embodiment, a system includes a catheter with a proximal section, a distal section, and a shaft coupled between the proximal section and the distal section. The system further includes a plurality of optical fibers located within the catheter, and a computing device coupled to the plurality of optical fibers. The computing device includes a memory and a processor configured to receive, from the optical fibers, optical measurement data of a portion of tissue during or after ablation. The processor of the computing device is further configured to identify one or more optical properties of the portion of tissue by analyzing the optical measurement data and detect a presence or an absence of a gap between one or more lesions formed in the portion of tissue based on the one or more optical properties.

In another embodiment, a computing device including a memory and a processor coupled to the memory is described. The processor of the computing device is configured to receive, from a catheter, optical measurement data of a portion of tissue while the catheter is moved along an ablation line in the portion of tissue, identify one or more optical properties of the portion of tissue by analyzing the optical measurement data, and detect a presence or an absence of a gap between one or more lesions formed in the portion of tissue based on the one or more optical properties.

Further features and advantages, as well as the structure and operation of various embodiments, are described in detail below with reference to the accompanying drawings. It is noted that the specific embodiments described herein are not intended to be limiting. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form a part of the specification, illustrate embodiments of the present disclosure and, together with the description, further serve to explain the principles of the disclosure and to enable a person skilled in the pertinent art to make and use the disclosure.

Embodiments of the present disclosure will be described with reference to the accompanying drawings.

DETAILED DESCRIPTION

Although specific configurations and arrangements are discussed, it should be understood that this is done for illustrative purposes only. A person skilled in the pertinent art will recognize that other configurations and arrangements can be used without departing from the spirit and scope of the present disclosure. It will be apparent to a person skilled in the pertinent art that this disclosure can also be employed in a variety of other applications.

It is noted that references in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases do not necessarily refer to the same embodiment. Further, when a particular feature, structure or characteristic is described in connection with an embodiment, it would be within the knowledge of one skilled in the art to affect such feature, structure or characteristic in connection with other embodiments whether or not explicitly described.

It should be noted that although this application may refer specifically to cardiac ablation, the embodiments described herein may target other pathologies as well, along with additional energy sources for ablation, including but not limited to cryogenic, radiofrequency (RF), microwave, laser, ultrasound, and pulsed electric fields. The principles of using energy to treat other pathologies are similar, and therefore the techniques used to apply the energy are similar.

Herein, the terms "electromagnetic radiation," "light," and "beam of radiation" are all used to describe the same electromagnetic signals propagating through the various described elements and systems.

Exemplary Catheter Embodiments

Figure 1:
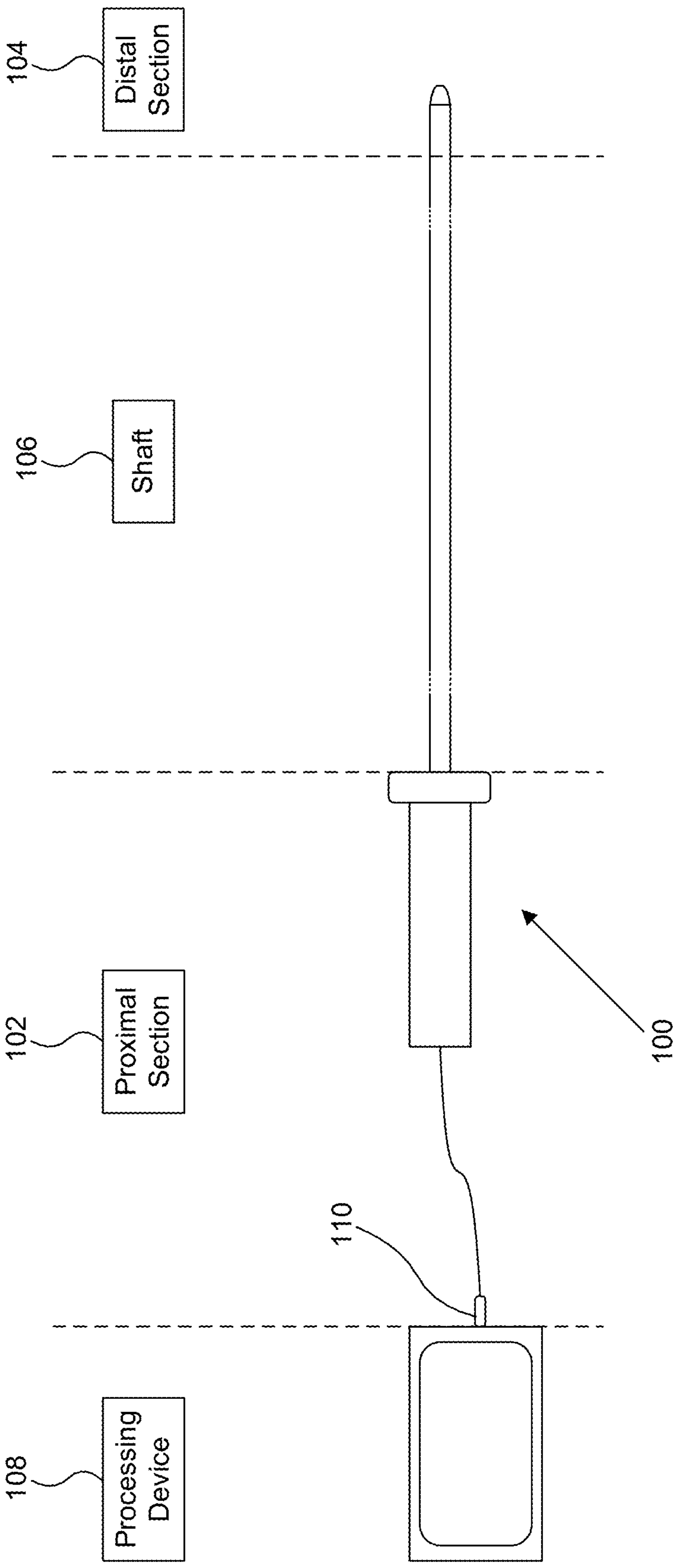
FIG. 1 illustrates an example diagram of a catheter, according to embodiments of the present disclosure.

FIG. 1 illustrates a catheter 100 according to embodiments of the present disclosure. Catheter 100 includes a proximal section 102, a distal section 104, and a shaft 106 coupled between proximal section 102 and distal section 104. In an embodiment, shaft 106 includes one or more radiopaque markers for navigation purposes. In one embodiment, catheter 100 includes a communication interface 110 between catheter 100 and a processing device 108. Communication interface 110 may include one or more optical fibers and connectors between processing device 108 and catheter 100. In other examples, communication interface 110 may include an interface component that allows wireless communication, such as Bluetooth, WiFi, cellular, and the like, to communicate with the catheter 100 or other processing components in a catheter system.

In an embodiment, shaft 106 and distal section 104 are disposable. As such, proximal section 102 may be reused by attaching a new shaft 106 and proximal section 104 each time a new procedure is to be performed. In another embodiment, proximal section 102 is also disposable.

Proximal section 102 may house various electrical and optical components used in the operation of catheter 100. A first optical source may be included within proximal section 102 to generate a source beam of radiation for optical evaluation. The first optical source may include one or more laser diodes or light emitting diodes (LEDs). The beam of radiation generated by the optical source may have a wavelength within the infrared range. In one example, the beam of radiation has a central wavelength of 1.3 μm. The optical source may be designed to output a beam of radiation at only a single wavelength, or it may be a swept source and be designed to output a range of different wavelengths. The generated beam of radiation may be guided towards distal section 104 via the optical transmission medium connected between proximal section 102 and distal section 104 within shaft 106. Some examples of optical transmission media include single mode optical fibers and/or multimode optical fibers. In one embodiment, the electrical transmission medium and the optical transmission medium are provided by the same hybrid medium allowing for both electrical and optical signal propagation.

In some embodiments, proximal section 102 may include a second optical source, such as a laser energy source, to generate laser energy that is applied at distal section 104 for tissue ablation. In some embodiments, the laser energy source may emit an ablation beam of laser energy at a wavelength of 980 nm or a wavelength of 1060 nm. The laser energy from the source in the proximal section 102 may propagate down the catheter 100 via an optical transmission medium connected between proximal section 102 and distal section 104 within shaft 106, and the laser energy may be output from the distal section 104 of catheter 100 to target tissue. For example, the laser energy from the source may produce an optical power of 5 W to 12 W that is applied to target tissue for 20-30 seconds to produce transmural lesions in heart tissue. In another example, the laser energy from the source may produce an optical power of 30 W to 70 W that is applied to target tissue for 60-90 seconds. In some embodiments, processing device 108 may include one or more components, such as detectors, electronics, and/or other components of an optical circuit/system as described herein. In other embodiments, these one or more components, such as detectors, electronics, and/or other components of an optical circuit/system may be included in the proximal section 102.

In an embodiment, proximal section 102 includes one or more components of an interferometer in order to perform low coherence interferometry (LCI) using the light generated from the second optical source. Due to the nature of interferometric data analysis, in an embodiment, the optical transmission medium used for guiding the light to and from distal section 104 does not affect the state and degree of light polarization. In another embodiment, the optical transmission medium affects the polarization in a constant and reversible way.

Proximal section 102 may include further interface elements with which a user of catheter 100 can control the operation of catheter 100. For example, proximal section 102 may include a deflection control mechanism that controls a deflection angle of distal section 104. The deflection control mechanism may require a mechanical movement of an element on proximal section 102, or the deflection control mechanism may use electrical connections to control the movement of distal section 104. Proximal section 102 may include various buttons or switches that allow a user to control when laser energy is applied at distal section 104, or when the beams of radiation are transmitted from distal section 104, allowing for the acquisition of optical data. In some embodiments, proximal section 102 may include a deflection control mechanism for controlling one or more pull wires that are coupled to the distal section 104. In some embodiments, deflection control mechanism and the one or more pull wires allow for steering of the distal section of catheter 100 in order to maneuver within and target specific tissue regions for ablation.

Distal section 104 includes a plurality of optical view ports. In some embodiments, the plurality of optical view ports may be referred to herein as orifices in the catheter tip. In an embodiment, one or more of the optical view ports are machined into the outer body of distal section 104. The optical view ports are distributed over the outside of distal section 104, resulting in a plurality of distinct viewing directions. In some embodiments, the optical view ports may transmit and collect light (e.g., optical signals) at various angles from the distal section 104. The optical view ports also allow for a plurality of directions (e.g., beam directions) in which laser energy may be directed for tissue ablation through one or more of the optical view ports. In an embodiment, each of the plurality of viewing directions are substantially non-coplanar. The optical view ports may also be designed with irrigation functionality to cool distal section 104 and surrounding tissue during ablation.

Figure 2A:
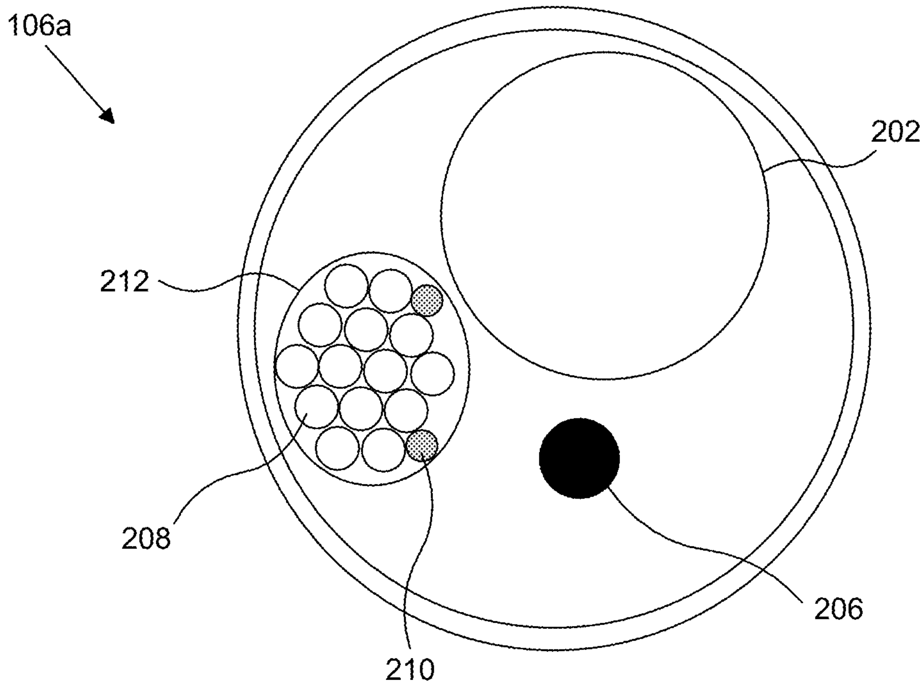
FIGS. 2A and 2B illustrate cross sections of a catheter, according to embodiments of the present disclosure.
Figure 2B:
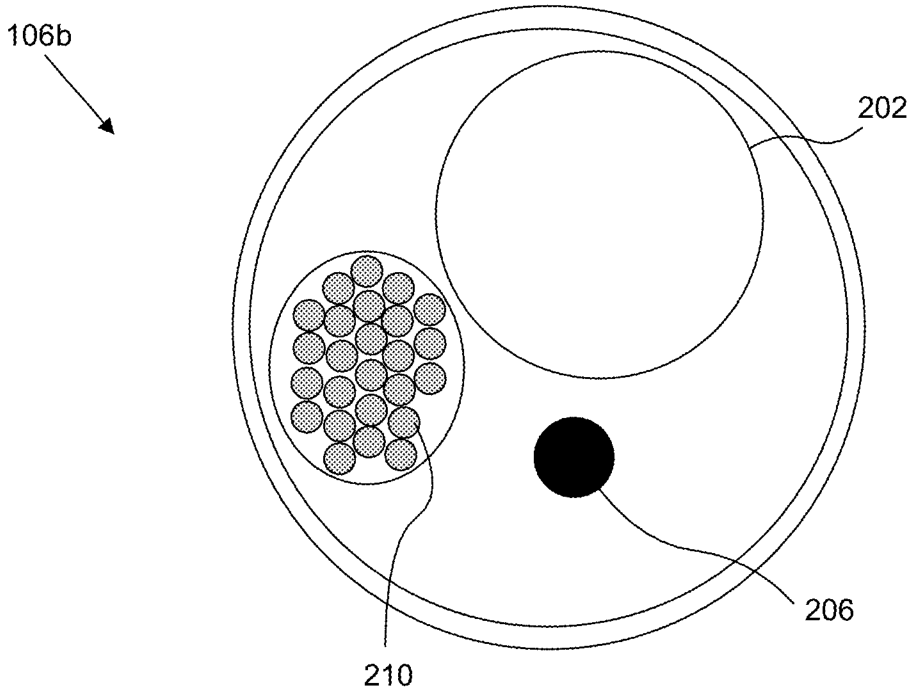

FIGS. 2A and 2B illustrate cross-section views of shaft 106, according to embodiments of the present disclosure. Shaft 106 may include all of the elements interconnecting proximal section 102 with distal section 104. Shaft 106*a* illustrates an embodiment that houses an irrigation channel 202, deflection mechanism 206, electrical connections 208, and optical transmission medium 210. FIG. 2A illustrates a protective cover 212 wrapped around both electrical connections 208 and optical transmission media 210. Electrical connections 208 may be used to provide signals to optical modulating components located in distal section 104. In other embodiments, optical transmission media 212 and components may be located within a protective cover that is separate from the protective cover 212 in which the electrical connections 208 is housed. One or more optical transmission media 210 guide light generated from the optical source (exposure light) towards distal section 104, while another subset of optical transmission media 210 guides light returning from distal section 104 (scattered or reflected light) back to proximal section 102. In another example, the same one or more optical transmission media 210 guides light in both directions. In some embodiments, the optical transmission medium 210 comprises one or more single mode optical fibers and/or multimode optical fibers.

Irrigation channel 202 may be a hollow tube used to guide cooling fluid towards distal section 104. Irrigation channel 202 may include heating and/or cooling elements disposed along the channel to affect the temperature of the fluid. In another embodiment, irrigation channel 202 may also be used as an avenue for drawing fluid surrounding distal section 104 back towards proximal section 102.

Deflection mechanism 206 may include electrical or mechanical elements designed to provide a signal to distal section 104 in order to change a deflection angle of distal section 104. The deflection system enables guidance of distal section 104 by actuating a mechanical control placed in proximal section 102, according to an embodiment. This system may be based on a series of aligned and uniformly spaced cutouts in shaft 106 aimed at providing unidirectional deflection of distal section 104, in combination with a wire which connects the deflection mechanism control in proximal section 102 with the catheter tip at distal section 104. In this way, a certain movement of the proximal section may be projected to the distal section. Other embodiments involving the combination of several control wires attached to the catheter tip may enable the deflection of the catheter tip along different directions.

FIG. 2B illustrates a cross-section of shaft 106*b*. Shaft 106*b* depicts an embodiment having most of the same elements as shaft 106*a* from FIG. 2A, except that there are no electrical connections 208. Shaft 106*b* may be used in situations where modulation (e.g., multiplexing) of the generated beam of radiation is performed in proximal section 102. In some embodiments, shaft 106*b* may be implemented in a diagnostic catheter that is used for laser or cryogenic ablation.

Exemplary System, Console, and Catheter Embodiments

In some embodiments, an ablation catheter and console system may use optical coherence tomography (OCT) and/or optical coherence reflectometry (OCR), refractometry, or other methods to perform tissue ablations and detect gaps between ablated and non-ablated tissue in real-time to assess lesion formation by directly observing the scar pattern in tissue. The methods, devices, and systems described herein acquire optically reflected/refracted light from the tissue, determine optical properties of the reflected light (e.g., by measuring intensity and polarization and computing phase retardation and/or birefringence of tissue based on the measurements), and provide a real-time assessment and visualization of tissue. By presenting a visualization of optical measurement data, the ablation catheter and console system may monitor changes, as these optical properties may change when tissue is scarred when compared to healthy tissue. By identifying the changes in optical properties of the tissue, gaps in between one or more lesions in ablated tissue may be detected.

In some embodiments, the devices and systems described herein may be used to perform tissue characterization of fibrosis, lesion formation, and the like and may evaluate various tissues, including fat tissue, thin tissue, scar tissue, capillaries, veins, blood vessels, blood, blood clots, nerve (e.g. for denervation), conductive tissue, and the like.

Figure 3:
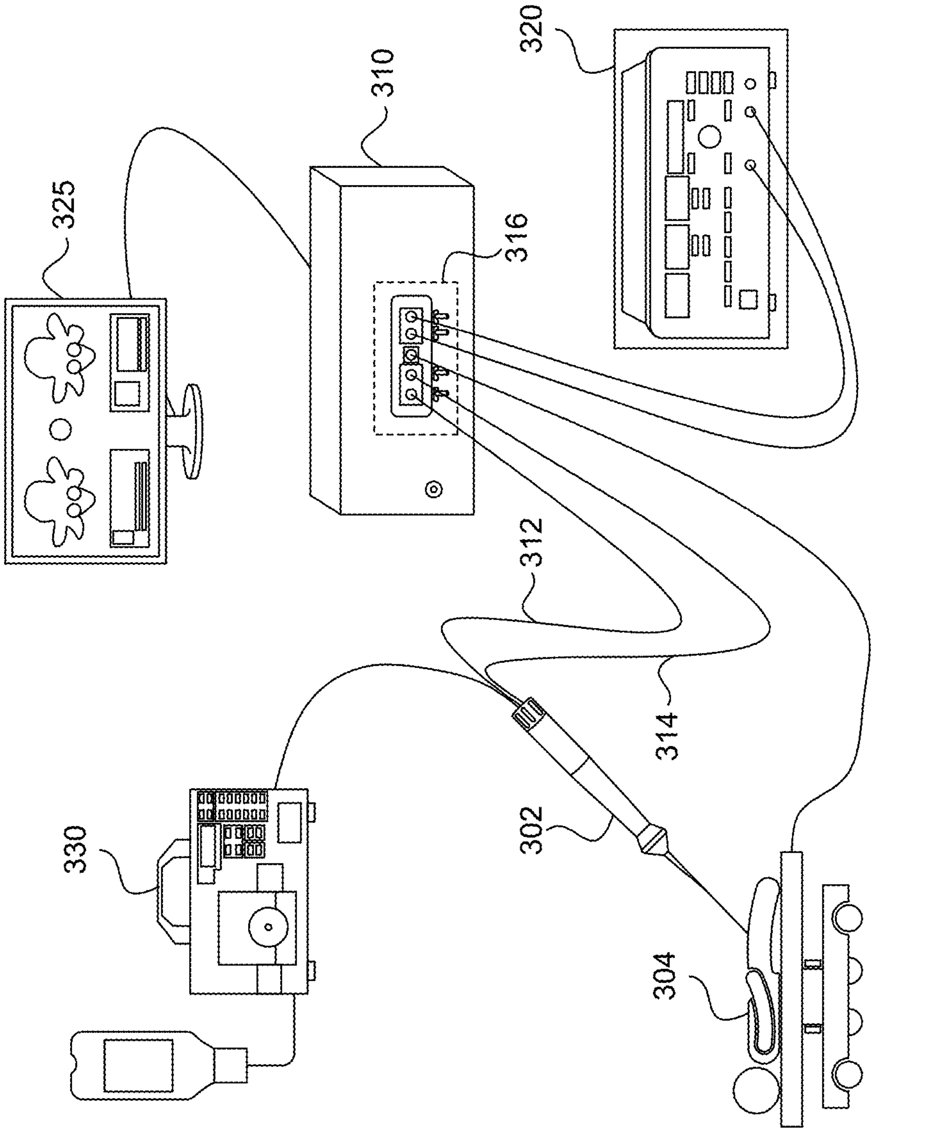
FIG. 3 illustrates an example diagram of a system for ablation and gap detection, according to embodiments of the present disclosure.

FIG. 3 illustrates an example diagram of a system 300 for performing ablation and gap detection, according to embodiments of the present disclosure. The system 300 includes catheter 302, console 310, signal generator 320, display 325, and irrigation pump 330. The catheter 302, console 310, signal generator 320, display 325, and irrigation pump 330 may be communicatively coupled together via wired and/or wireless connections. In some embodiments, catheter 302 may represent an exemplary embodiment of catheter 100 shown in FIG. 1. In some embodiments, a distal section of catheter 302 is positioned at a portion of tissue in patient 304. In some embodiments, one or more optical ports in the distal section of catheter 302 may be positioned to be in contact with the portion of tissue in patient 304. It is understood that the embodiments described herein may be used in vivo and/or in vitro.

In some embodiments, catheter 302 may be positioned at a portion of tissue subject to ablation using energy generated by signal generator 320. In some embodiments, signal generator 320 may be an electronic device configured to generate radiofrequency (RF), cryogenic, or electroporation (e.g., pulsed electric field) signals for ablation. In some embodiments, the signal generator 320 may be referred to herein as an ablation energy source. The signal generator 320 may be coupled to catheter 302 directly or via the console 310, and may send energy to catheter 302 to ablate the portion of tissue at a selected tissue site. In some embodiments, the portion of tissue may comprise myocardial tissue, cardiac muscle tissue, skeletal tissue, or the like. Energy may be applied to the portion of tissue through optical view ports in the distal section of catheter 302. After applying the energy, structural changes in the tissue may be observed by acquiring optical signals via one or more optical view ports of catheter 302.

Console 310 may comprise a computing device configured to acquire the optical signals from catheter 302 and analyze the optical signals to detect changes in optical properties of the tissue. In some embodiments, console 310 may include hardware (e.g., circuits), firmware, software, or any combination thereof to perform analysis of the optical signals and gap detection as described herein. In some embodiments, console 310 may send light through an optical circuit within itself and the catheter 302 and into the tissue to monitor scar progression, contact between the tissue and catheter 302, and other characteristics of the tissue. In some embodiments, console 310 may be referred to herein as a control console, a computing device, a processing device, and/or controller. Console 310 may be coupled to display 325, which may provide a visualization of optical signals acquired from tissue in real-time or near real-time to a user. In some embodiments, the display 325 may present results from the optical signal analysis and gap detection and allow a user to select/view, modify, and/or control parameters related to operation of catheter 302, console 310, signal generator 320, and/or irrigation pump 330. In some embodiments, the display 325 may be referred to herein as a user interface. In some embodiments, the display 325 may send auditory, visual, and/or tactile data to a user to inform him or her of the characteristics of a tissue sample and status of the ablation system and treatment variables, before, during, and/or after ablation energy is delivered. In some embodiments, the data provided by the display 325 may be used by clinicians to make better informed decisions on ablation treatments.

In some embodiments, irrigation pump 330 may be coupled to catheter 302 via a tubing. In some embodiments, irrigation pump 330 may allow for fluid to be pumped through the tubing and released at the tissue site through catheter 302 (e.g., through optical view ports or through separate irrigation slits at the distal section of catheter 302). Fluid from the irrigation pump 330 may cool the distal section of catheter 302 and the surrounding tissue during ablation, and also flush away any debris during and/or after ablation. In some embodiments, the irrigation pump 330 may be referred to herein as a cooling source.

In some embodiments, catheter 302 may be coupled to console 310 via one or more optical connections 312 and one or more electrical connections 314. Optical connections 312 may include single mode optical fibers and/or multimode optical fibers that allow acquisition and/or transmission of optical signals to and from catheter 302 and console 310 for further analysis. Electrical connections 314 may include wiring, pins, and/or components used for supplying power and energy from signal generator 320 to catheter 302 for ablation.

In some embodiments, the optical and electrical connections 312, 314 may be connected to console 310 via a communication interface 316. Communication interface 316 may allow for transmission of various signals (e.g., optical and electrical signals) between catheter 302 and console 310. In some embodiments, the communication interface 316 may include a connector that facilitates proper alignment of optical fibers between the catheter 302 and console 310. In some embodiments, the connector design may include both electrical and optical extension lines.

Figure 4:
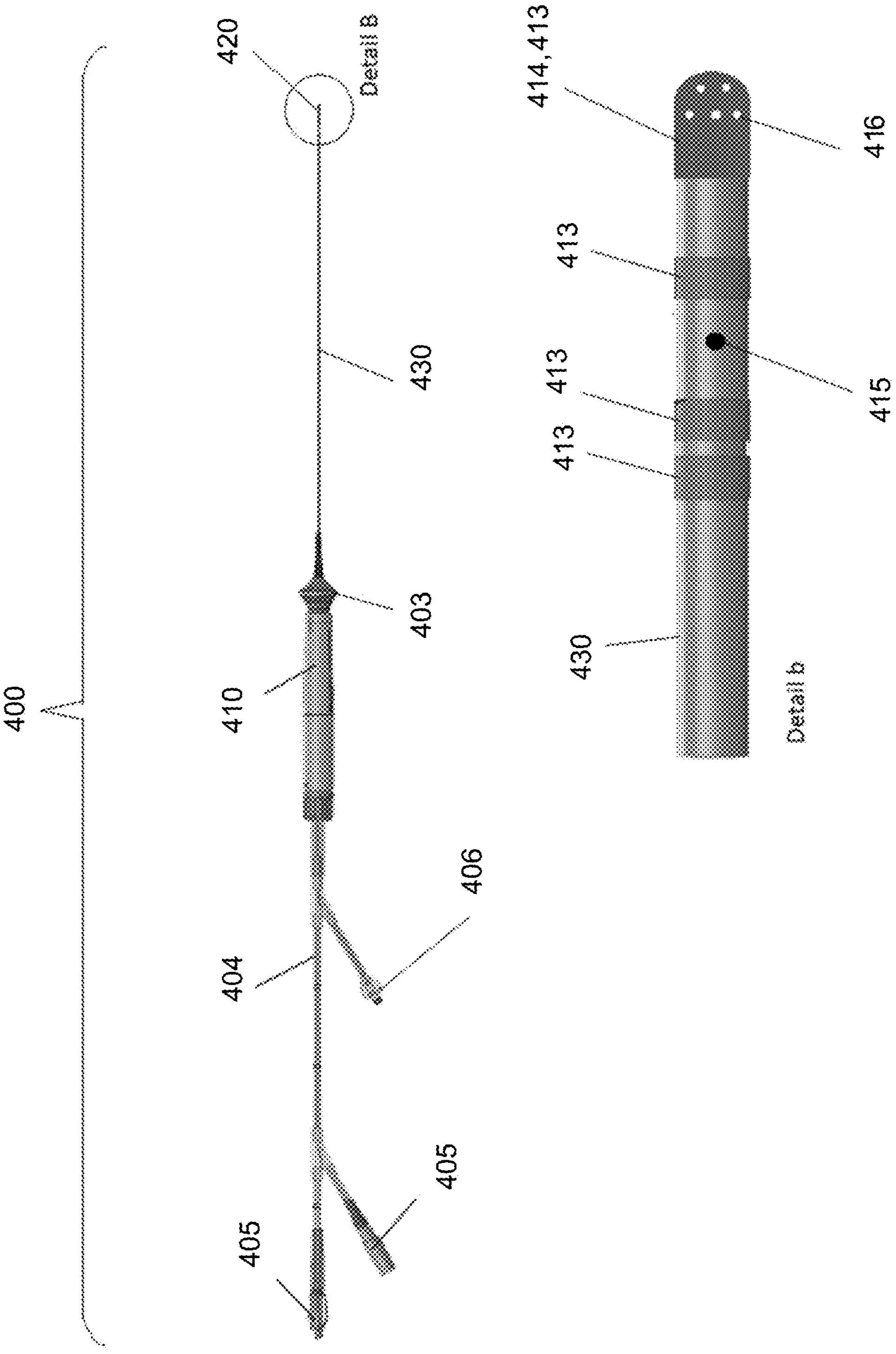
FIG. 4 illustrates a diagram of example components of a catheter that may be used for controlled ablation, according to embodiments of the present disclosure.

FIG. 4 illustrates an example diagram of catheter 400, according to embodiments of the present disclosure. Catheter 400 represents an exemplary embodiment of catheter 100 and catheter 302 shown in FIGS. 1 and 3, respectively. Catheter 400 includes a proximal section 410, a distal section 420, and a shaft 430 coupled between proximal section 410 and distal section 420. In some embodiments, the proximal section 410 includes a handle to interface with a clinical user. The handle may include one or more buttons, sliders, levers, lights, dials and other elements that allow for mechanical and functional control of the catheter shaft 430 and the distal section 420. In some embodiments, the proximal section 410 of the catheter may also include wiring 404 and one or more connectors 405. The wiring 404 may include a wire harness or grouped cables and optical fibers and/or wave guides. The one or more connectors 405 may serve as an interface for the catheter 400 and connect the catheter 400 directly or indirectly to other elements of the ablation system, including the signal generator 320, an optical source, console 310 and/or display 325. In some embodiments, the proximal section 410 of the catheter may also have a port to connect to the irrigation pump 330. In some embodiments, the wiring 404, wiring harness elements, and one or more connectors 405 may be detachable from the handle in the proximal section. In other embodiments, communication between the catheter 400 and other elements of the ablation system may be wireless, using technologies such as Bluetooth, WiFi, cellular, etc.

Proximal section 410 may include further interface elements, with which a user of catheter 400 can control the operation of catheter 400. For example, proximal section 410 may include a deflection control mechanism that controls a deflection angle of distal section 420. The deflection control mechanism may use a mechanical movement of an element on proximal section 410, or the deflection control mechanism may use electrical connections to control the movement of distal section 420. Proximal section 410 may include various buttons or switches that allow a user to control when RF energy is applied at distal section 420, or when beams of radiation and/or light are transmitted from distal section 420, allowing for the acquisition of optical data. In some embodiments, these buttons or switches may be located at a separate user interface coupled to a processing device or the handle itself.

The deflection control mechanism may include electrical or mechanical elements designed to provide a signal to distal section 420 in order to change a deflection angle of distal section 420. The deflection system enables guidance of distal section 420 by actuating a mechanical control placed in proximal section 410, according to an embodiment. This deflection system may be based on a series of aligned and uniformly spaced cutouts in catheter shaft 430 aimed at providing unidirectional or multidirectional deflection of distal section 420, in combination with a wire that connects the deflection mechanism control in proximal section 410 with the catheter tip 414 at distal section 420. In this way, a certain movement of the proximal section 410 may be projected to the distal section 420. In some embodiments, the combination of several control wires attached to a catheter tip may enable the deflection of the catheter tip along different directions.

FIG. 4 further illustrates elements of the distal section 420 in an expanded view showing the catheter tip 414. In an embodiment, shaft 430 and distal segments of the catheter may include one or more radiopaque markers 415 for navigation purposes. Distal section 420 may include one or more external electrodes 413 for ablation, according to some embodiments. The electrodes 413 may be distributed over segments of the distal section 420 of the catheter or directly on the catheter tip 414 at the distal end of the distal section 420. In some embodiments, where cooling is needed, the distal section 420 of the catheter 400 may also include one or more irrigation orifices 416. In some embodiments, cooling fluids (e.g., compressible and/or incompressible) provided by the irrigation pump 330 travel through a channel partially at least through the shaft 430 of the catheter 400 and are then externalized through the irrigation orifices 416. These irrigation orifices 416 can be located in any segments of the catheter shaft 430, electrodes 416, or catheter tip 414.

Figure 5A:
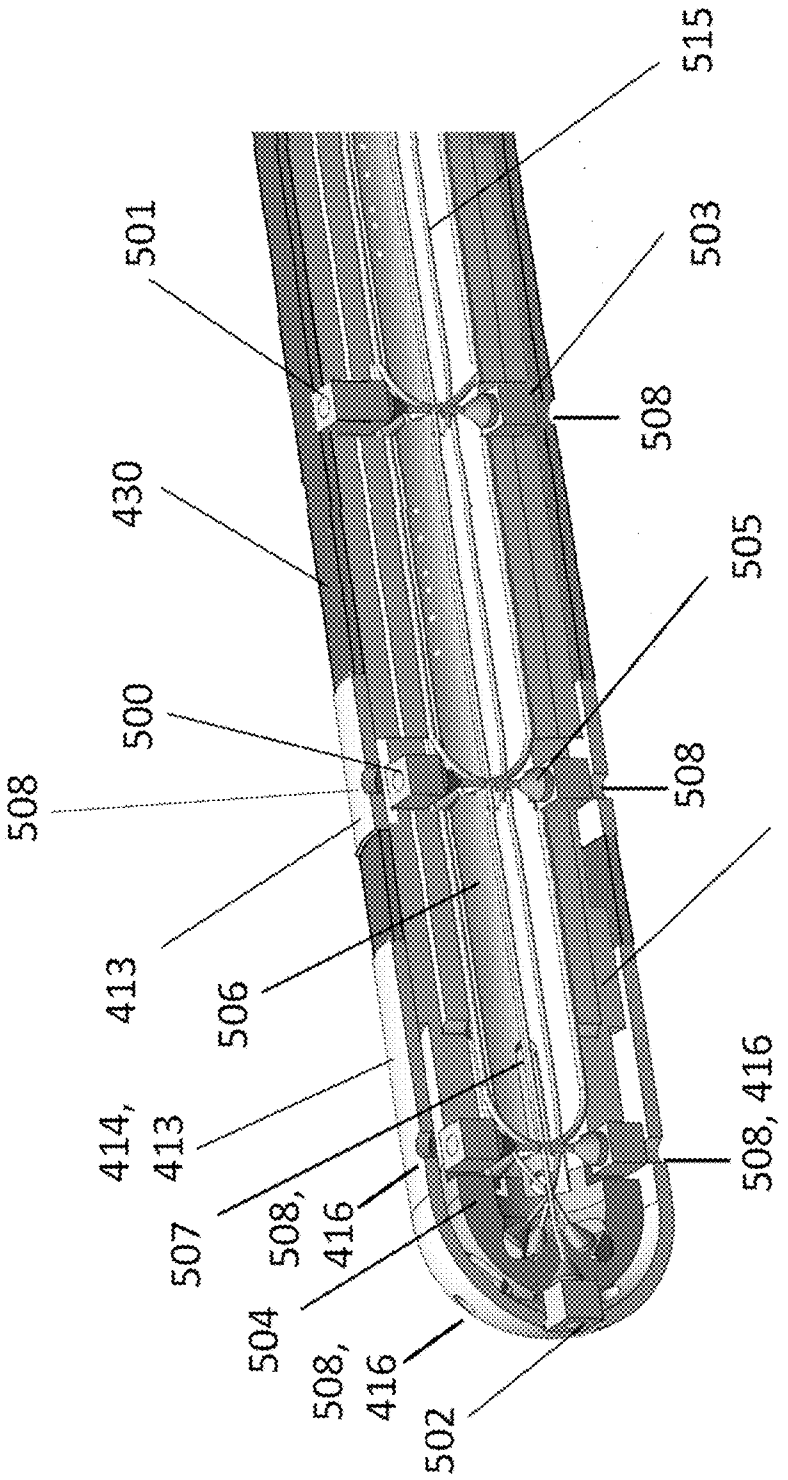
FIG. 5A illustrates a diagram showing an example axial cross-section view of a distal segment of a catheter, according to embodiments of the present disclosure.
Figure 5B:
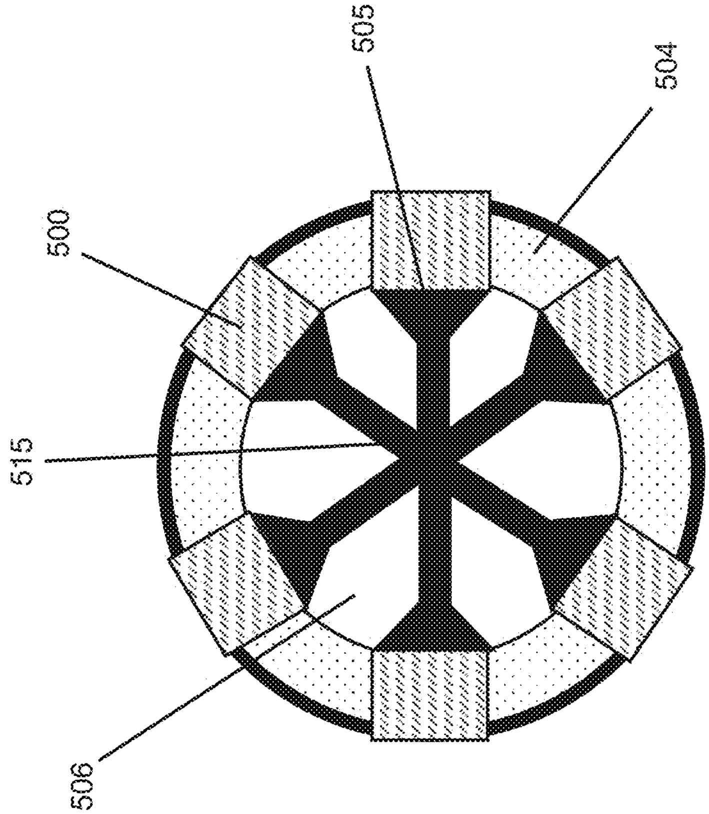
FIG. 5B illustrates a diagram showing an example radial cross-section view of a distal segment of a catheter, according to embodiments of the present disclosure.

FIGS. 5A and 5B illustrate diagrams of an example axial cross-section view and a radial cross section view, respectively, of a distal segment of catheter 400, according to embodiments of the present disclosure. FIGS. 5A and 5B illustrate different configurations of electrodes, view ports, and lens-fiber assemblies in the catheter tip.

As shown in FIGS. 5A-5B, the distal section 420 of the catheter and shaft 430 may have a single electrode or multiple electrodes 413 to deliver ablation energy. In some embodiments, PFA energy may be used, and the electrode 413 configuration may be configured to deliver monophasic or biphasic pulse applications. In some embodiments, where cooling is implemented, a central cooling channel 506 and cooling communication paths 507 may guide cooling fluid through the shaft 430 to the distal section 420, and such fluid may then be externalized through irrigation orifices 416 to cool down surrounding tissues or blood.

Distal section 420 may also include a plurality of optical view ports 508 to transmit/collect light at various angles from distal section 420. In some embodiments, the optical view ports 508 may be distributed over the outside of distal section 420, resulting in a plurality of distinct viewing directions, In some embodiments, each of the plurality of viewing directions is substantially non-coplanar.

In some embodiments illustrated in FIGS. 5A-5B light is transported through the shaft 430 and distal section 420 by optical fibers 505. Such optical fibers 505 may be coated or uncoated. In some embodiments, optical fibers 505 are coated with a polymer for protection, insulation and structural integrity. In some embodiments, optical fibers 505 are attached to lenses 500 to focus the light that will then go into the tissue. In some embodiments the fibers may be attached mechanically or chemically through glue or adhesives 505. In some embodiments, the glue or adhesives 505 may be selected to provide mechanical strength and also optical index matching. As illustrated in FIG. 5B, in some embodiments, the lenses 500 and/or fibers 505 may be supported by an internal support structure 504 to localize and orient lenses 500 and fibers 505 in place. In other embodiments, the lenses 500 may be localized and/or oriented by the configuration of the shaft 430, electrodes 413, and the catheter tip 414. In some embodiments, the lenses 500 might not be external elements to the fibers 505, but may be created by curvatures manufactured (e.g., etched, machined, laser cut, or chemically formed) directly onto the distal end of the fiber 505 and the fiber core. In some embodiments, the distal section 420 may include a substrate with patterned waveguides and optical focusing or directing elements (e.g., lenses, mirrors, and the like) for guiding light to/from each of the plurality of optical view ports 508. The substrate may be a flexible or partially flexible substrate made from a material such as polyimide, polyethylene glycol, Parylene, or polydimethelsiloxane (PDMS).

In some embodiments, as shown in FIG. 5A, lenses 500 may be connected to optical fibers and placed within recesses 503 in the catheter. In some embodiments, lenses may be flush 501 with the catheter surface (e.g., shaft, electrodes, or tip), or may extend beyond surface 502 of the catheter shaft 430, electrodes 413, or tip 414. In some embodiments, lenses that are flush 501 with the catheter surface or extend beyond the surface 502 may be a contact point with the external tissue. In some embodiments, where cooling is implemented, lenses that are recessed into the catheter and use view ports 508 to allow for passage of light, may also use these same view ports 508 as irrigation orifices 416. In some embodiments, view ports 508 and irrigation orifices 416 may be distinct and separate elements.

Exemplary Optical System Embodiments

Figure 6:
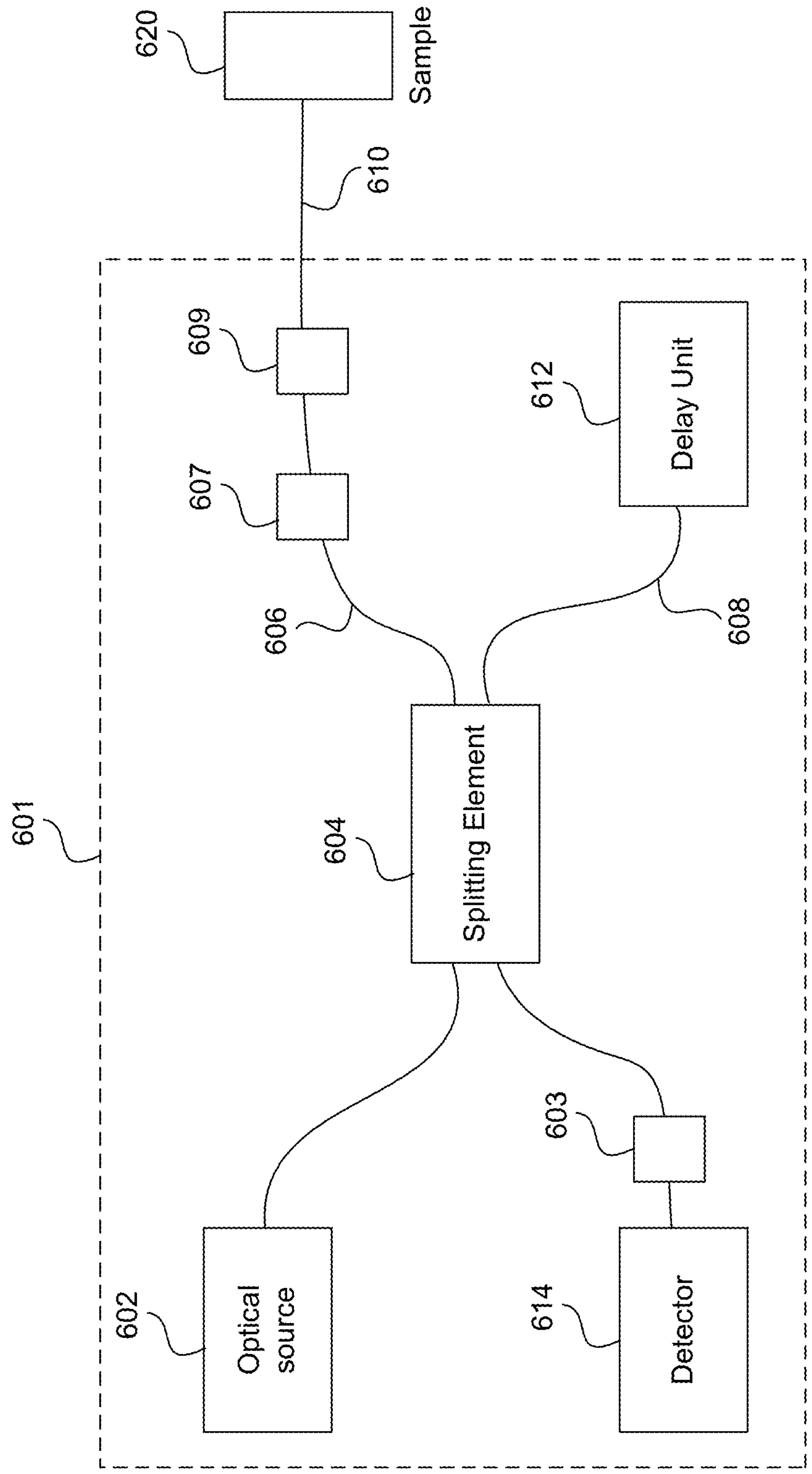
FIG. 6 illustrates an example diagram of an optical system for imaging a sample, according to embodiments of the present disclosure.

FIG. 6 illustrates a diagram of an example optical system 601 for imaging a sample 620, according to embodiments of the present disclosure. In some embodiments, the components of optical system 601 may be implemented in console 310 to acquire optical measurements of the sample 620 using catheter 100, 302, or 400. In some embodiments, optical system 601 may be referred to herein as an optical circuit. In some embodiments, sample 620 may be a tissue surface within a patient's body.

In some embodiments, optical system 601 may utilize low-coherence interferometry (LCI), optical coherence tomography (OCT), and/or optical coherence refractometry or other optical modalities to perform imaging. Optical system 601 may include optical source 602, polarization splitter 603, coupling/splitting element 606, sample arm 606, polarization switch 607, reference arm 608, optical switch 609, output fibers 610, delay unit 612, and detector 614. It should be understood that optical system 601 may include any number of other optical elements not shown for the sake of clarity. In some embodiments, optical system 601 may include mirrors, lenses, gratings, splitters, micromechanical elements, and the like, along the paths of sample arm 606 or reference arm 608.

Optical source 602 may include one or more laser diodes or light emitting diodes (LEDs). For example, LEDs may be used when performing time domain and/or spectral domain analysis, while tunable lasers may be used to sweep the wavelength of the light across a range of wavelengths. The beam of radiation generated by the optical source 602 may have a wavelength within the infrared range (e.g., 750 nm to 1 mm), while other optical sources 602 may work within the visible range (e.g., 400 nm to 750 nm) or ultraviolet range (e.g., 400 nm to 10 nm). In an example, the beam of radiation has a central wavelength between 1000 nm and 1600 nm. The optical source 602 may be designed to output a beam of radiation at only a single wavelength, or it may be a swept source and be designed to output a range of different wavelengths. The range of wavelengths may include any wavelengths found in the near-infrared or mid-infrared spectral range. The generated beam of radiation may be guided towards distal section 420 via an optical transmission medium connected between proximal section 410 and distal section 420 within shaft 430.

In some embodiments, the optical system 601 includes one or more components of an interferometer in order to perform LCI using the light generated from the optical source 602. In some embodiments, in performing LCI, the optical system 601 may analyze interferometric data. The interferometric data analysis may be associated with understanding changes in the polarization state of light reflected or scattered by the tissue, which may allow assessment of changes in the birefringence of tissue. In some embodiments, the optical transmission medium used for guiding the light to and from distal section 420 might not affect the state and degree of light polarization (e.g., single mode optical fiber). In other embodiments, for such a LCI circuit, the optical transmission medium may affect the polarization in a constant and reversible way. In further embodiments of the optical system 601, optical analysis of the light reflected or scattered back by the tissue may include methods associated with tissue spectroscopy. With tissue spectroscopy, the optical transmission medium used for guiding the light to and from distal section 420 may allow for multiple modes of light, such as a multi-mode optical fiber. In further embodiments of the optical system 601, both single mode fibers and multi-mode fibers may be used to determine different paths from one or more optical sources to the distal section 420 and back, so that both LCI methods and spectroscopy methods may be used by the system to better control the ablation procedure.

Various embodiments of the present disclosure include a LCI system integrated within a medical device such as catheter 400 for optical interrogation of a sample 620 (e.g., at an ablation tissue site). In some embodiments, the LCI system may be implemented by optical system 601, and the optical system 601 may be referred to herein as an LCI system.

In some embodiments, optical source 602 may generate a source beam of radiation that is coupled to coupling/splitting element 604 via one or more fibers. Coupling/splitting element 604 is used to direct light received from optical source 602 to both sample arm 606 and reference arm 608. Coupling/splitting element 604 may be, for example, a coupling element (e.g., a bi-directional coupler), an optical splitter, an adjustable splitting-ratio coupler, or any other modulating optical device that converts a single beam of light into two or more beams of light. In some embodiments, the light from the optical source 602 may also go through an optical attenuator.

Light that travels down sample arm 606 ultimately impinges upon sample 620 by traveling through a polarization switch 607 and an optical switch 609. In some embodiments, polarization switch 607 may be included on the sample arm 606 but may also be at the input of the LCI system (e.g., prior to the splitting/coupling element 606). In some embodiments, after passing through the polarization switch 607, the optical switch 609 may direct the light to one or more of the multiple output fibers 610. In some embodiments, the multiple output fibers 610 represent the fibers at the console 310 that are coupled to fibers of the catheter 302 via a connector.

In some embodiments, sample 620 may be any suitable sample to be imaged, such as tissue. The light scatters and reflects back from various depths within sample 620 and the scattered/reflected radiation is collected back into sample arm 606. The scan depth may be chosen via the delay imposed on the light within delay unit 612.

In some embodiments, a delay unit 612 may include various light modulating elements. These modulating elements may perform phase and/or frequency modulation to counteract undesired optical effects in the light, and to select one or more depths of sample 620 to be imaged. In some embodiments, the delay unit 612 may also control the light polarization of the reference arm and modulate the polarization. In some embodiments, the modulation schemes on the reference arm 608 may simplify the need of a switching element in the reference arm, and may allow a shift from time-multiplexing to frequency/phase/code/polarization multiplexing. The use of the term "light" may refer to any range of the electromagnetic spectrum. In an embodiment, the term "light" refers to infrared radiation at a wavelength of about 1.3 μm.

In the embodiment shown, delay unit 612 is located within reference arm 608. However, it should be understood that delay unit 612 may instead be located in sample arm 606. Alternatively, various elements of delay unit 612 may be present in both sample arm 606 and reference arm 608. For example, elements of delay unit 612 that introduce a variable delay to the light may be located in sample arm 606, while elements that modulate different polarization modes of the light may be located in reference arm 608. In another example, elements of delay unit 612 that modulate different polarization modes of the light may be located in sample arm 606, while elements that introduce a variable delay to the light may be located in reference arm 608. In one example, sample arm 606 and reference arm 608 are optical fibers. Other implementations may be considered as well, such as, for example, fiber optic systems, free-space optical systems, photonic integrated circuits, etc.

In an embodiment, light may be coupled from optical source 602 to coupling/splitting element 604 via one or more fibers, and light may be coupled from coupling/splitting element 604 to polarization splitter 603 to detector 614 via one or more fibers or by direct free-space coupling.

In some embodiments, optical switch 609 allows for selection of one or more beams through the multiple output fibers 610. In some embodiments, one beam may be active at a time, such that the signal coming back from the sample 620 may be combined with the reference arm 608 and then split into different channels in detector 614 using a polarization splitter 603. In some embodiments, this may allow birefringence and other optical properties of the tissue to be measured from one channel at a time. In other embodiments, several beams may be active at the same time and split by a multiplexer or other type of beam splitter, in which each beam from each path is discerned by their frequency, wavelength, amplitude, or other optical characteristics of the beam's light.

In some embodiments, the light within sample arm 606 and reference arm 608 is recombined by coupling/splitting element 604 (or by a different optical coupling element) and then split by polarization splitter 603 before being received at detector 614. In some embodiments, the light may be polarized prior to coupling by the coupling/splitting element 604. In other embodiments, the light may be split in the reference arm 608. Detector 614 may include any number of photodiodes, charge-coupling devices, and/or CMOS structures to transduce the received light into an electrical signal. The electrical signal contains depth-resolved optical data related to sample 620 and may be received by a processing device for further analysis and signal processing procedures. As used herein, the term "depth-resolved" defines data in which one or more portions of the data related to specific depths of an imaged sample can be identified. In some embodiments, the processing device has an interface that converts such electrical signals into digital data that can then be processed and analyzed by a standard processing unit such as a computer, a data processor, reprogrammable hardware, ASICs or any other types of digital data processing circuits or systems.

In some embodiments, optical source 602, detector 614, and delay unit 612 are located within proximal section 410 of catheter 400. In some embodiments, optical source 602, detector 614, and delay unit 612 are located within processing device 108. Coupling/splitting element 604, polarization splitter 603, polarization switch 607, optical switch 609, and at least part of one or both of sample arm 606 and reference arm 608 may be located in processing device 108 or in either proximal section 102 or distal section 104 of catheter 100. In some embodiments, any of the elements of optical system 601 are located in processing device 108 or in the console 310 of the catheter system 300 shown in FIG. 3. In some embodiments, detector 614 may be located in a handle of the catheter 100, whereas and source 602 may be located in processing device 108. In some embodiments, any of the components of optical system 601 are located external to catheter 100 or catheter 302, for example, within processing device 108 or within console 310. In some embodiments, optical system 601 is illustrated as an interferometer design similar to a Michelson interferometer. However, other interferometer designs are possible as well, including Mach-Zehnder or Mireau interferometer designs. In some embodiments, the components in optical system 602 may be adapted for a spectral-domain OCT configuration. For example, optical source 602 may be a super-luminescent diode (SLED) or light-emitting diode (LED), and detector 614 may be a spectrometer in order to conduct optical spectroscopy of tissue.

Exemplary Gap Detection Embodiments

The catheter and console systems described herein allow for gap detection between ablated and non-ablated tissue to assess proper lesion formation. In some embodiments, a clinician or user may perform cardiac ablation using a catheter (e.g., catheter 400) along an ablation line in cardiac tissue. In some embodiments, the ablation line may include a plurality of ablation points in the portion of tissue where ablation energy has been applied to the tissue by the catheter. In some embodiments, ablation lines may be created by the catheter to isolate different segments of the left atrium and electrically isolate the pulmonary veins. For example, these lines may be created along the roof of the left atrium between the right and left upper pulmonary veins and from the mitral valve to the left inferior pulmonary vein. While isolating pulmonary veins using ablation lines in an initial procedure may be beneficial for treating atrial fibrillation, recurrences of atrial fibrillation after ablation may be common. Recurrence may occur if pulmonary veins that were isolated during an initial procedure do not remain isolated, resulting in the restoration of conduction which can be a main contributor for recurring arrhythmias. In some cases, the restoration of conduction across ablation lines may occur as a result of gaps in the ablation lines. Gaps may be tissue regions that have not formed a lesion, or have not formed a sufficiently large lesion, after ablative energy has been applied. For example, a gap may exist between one or more lesions formed in the ablation line in a portion of tissue. Gaps may lead to discontinuous ablation lines, which may cause conduction, which may in turn result in a recurrence of arrhythmias.

Thus, it would be beneficial for a user performing ablation to have the capability to check lesion formation during an ablation procedure and assess for any gaps. In particular, it may be beneficial for the user to have a gap detection functionality in the catheter and console system (e.g., catheter 302 and console 310 in system 300) in order to identify gaps while the user is performing ablation and identify locations in the tissue that may need to be re-ablated. Accordingly, the systems, methods, and devices described herein may provide an optical readout and visualization of tissue that can be monitored by changes in birefringence of the interrogated tissue to assess lesion formation and check for gaps. The systems described herein may generate visualization presented on a user interface shown on a display (e.g., display 325) in order to observe ablation lesions in real time and characterize or evaluate ablated areas for gap detection.

In some embodiments, a clinician or user may introduce a catheter device (e.g., catheter 100, 302, or 400) into the human vasculature directly or through an access sheath for performing ablation. The distal section 420 of the catheter is moved to the site of ablation using guide wires, access sheaths, steerable sheaths, or deflection of the catheter 400 itself. At the ablation site (e.g., atrium, ventricle, artery, vein, etc.), at least one or multiple electrodes 413 on the surface of the catheter distal section 420 are placed in direct contact with the tissue at the ablation site. Using light or other forms of radiation emitted by optical source, which travels at least partially through PM optical transmission media to the distal section 420 of the catheter 400, contact or contact stability may be established between the distal section 420 and tissue ablation site. After contact or contact stability is established, a PFA pulse train may be transmitted to the tissue, in which the characteristics of the pulse train (e.g., frequency, amplitude, intensity, or duration) are determined by the user.

During and/or after delivery of the ablation pulse train, changes in birefringence of the interrogated tissue may be monitored by the console 310 and display 325 through assessment of changes in the polarization state and phase retardation of the reflected/scattered light signal, sent into the tissue through the catheter. Birefringence is the optical property of a material, which is associated with the polarization and propagation direction of light. Most viable human soft tissue are generally considered to be birefringent (e.g., myocardium, renal, brain tissue, and the like). This birefringence comes from the organization and geometry of their internal components and structures. Most notably, the organization and geometry of proteins, and/or the organization and alignment of cells within a tissue, are significant determinants of tissue birefringence. Optical birefringence changes in tissue when some of its internal proteins pass from their normal state to a denatured state as the geometry of the proteins themselves and their arrangement within a matrix, changes. Collagen, elastin and fibrin are extracellular matrix proteins that when denatured can affect the birefringence property of a tissue, as the light reflected or scattered from such extracellular matrix may have a different polarization state (e.g., polarization and phase retardation) when compared to the optical signal received when these proteins are in a normal state. Further, other proteins in the cellular membrane and the intracellular cytoskeleton when denatured may also generate a change in the polarization state of light when denatured, or when the geometry of the cellular membrane or cytoskeleton changes, affecting the anisotropy of the tissue.

Experimentation using the LCI system described herein (e.g., using console 310 and optical system 601) has shown to be sensitive to changes in birefringence of tissue associated with application of a PFA energy train in absence of thermal damage. Therefore, the catheter system as described herein uses polarization-sensitive LCI to interrogate the optical state of an ablated sample and allow direct visualization in real-time of tissue by analyzing the signal of the reflected and scattered light and its polarization state, phase retardation, and birefringence. The catheter and console systems may provide users with direct visualization of lesions in tissue, along with detection of non-ablated tissue regions and permanently ablated tissue regions that will not have cardiac rhythm electrical conductivity. Determining and visualizing lesion geometry may allow for the clinician to assess if the lesion has fully penetrated the tissue wall or reached the desired structures at the site of ablation and if there are gaps in the ablation line.

In some embodiments, the catheter and console system may use birefringence signals obtained from analyzing optical measurement data of a portion of tissue to determine contact of the catheter with tissue and/or contact stability. In some embodiments, contact or contact stability of the catheter with tissue may be established, when at least one optical view port receives a birefringence signal when in contact with non-ablated tissue. Thus, the receiving of birefringence signals via the optical view ports (e.g., view ports 508) in the catheter may indicate that the distal section of the catheter is in contact with the portion of tissue to be ablated.

In some embodiments, the catheter and console system may perform gap detection by analyzing optical measurement data, and/or also by means of assessing ablation energy levels (e.g. comparing current sent in with current coming back). In some embodiments, the catheter and console system may compare a first level of ablation energy transmitted to a portion of tissue with a second level of energy reflected or otherwise returned to the system. Regardless of the type of ablation energy used (e.g., RF, PFA, etc.), the level of birefringence shown by permanently ablated (i.e., dead) tissue is different from the level of xc birefringence shown by live or partially ablated tissue. In particular, ablated tissue may exhibit little or no birefringence. Live or partially ablated birefringence may show increased levels of birefringence.

Figure 7:
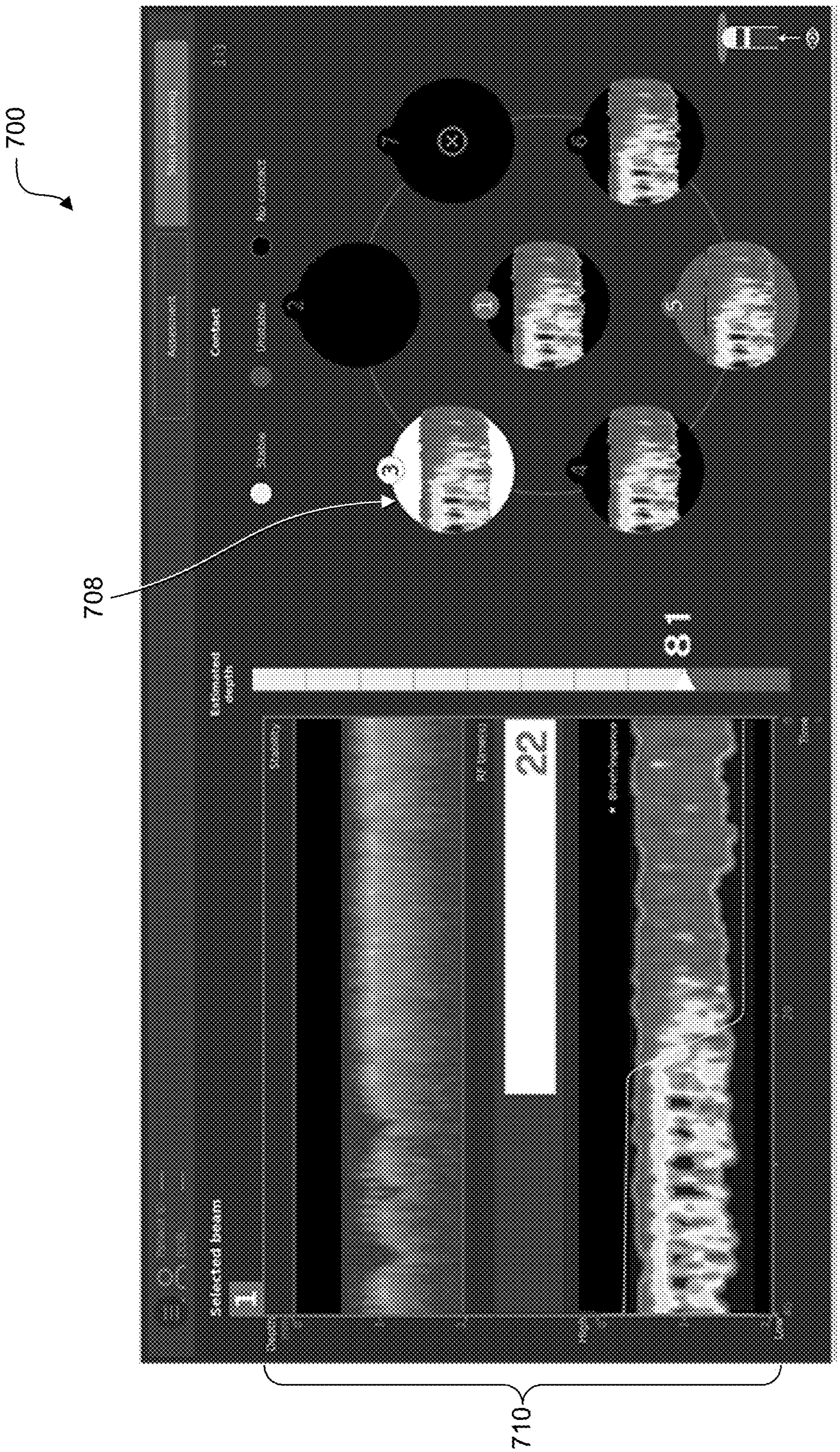
FIG. 7 illustrates an example graphical user interface (GUI) showing a visualization of gap detection based on birefringence, according to embodiments of the present disclosure.

FIG. 7 illustrates an example graphical user interface (GUI) 700 showing a visualization of optical measurement data, according to embodiments of the present disclosure. In some embodiments, the GUI 700 may be presented on display 325 coupled to console 310, in which optical measurement data may be obtained by optical system 601. The GUI 700 provides optical measurement data, for example as processed by console 310, in real-time or near real-time for an ablation process. In some embodiments, the GUI 700 includes a front view of the catheter tip (shown on the right side of the GUI 700) showing different sections, such as a plurality of tiles 708, corresponding to the various optical view ports (e.g., view ports 508) in the catheter tip.

In some embodiments, the plurality of tiles 708 in GUI 700 may show the optical readout for each optical view port in the catheter. In some embodiments, the plurality of tiles 708 may each correspond to a different optical view port of the catheter tip. Each tile 708 may represent the birefringence signal resulting from processing, by the console, the optical signal and/or optical measurements obtained from a respective optical view port section in the catheter. In some embodiments, individual tiles 708 may be switched on or off (or may appear or disappear) based on a particular optical view port section being active at a given time. In some embodiments, the tiles 708 may show which optical view ports are in contact with tissue and which beams from the different optical view ports are in operation. In some embodiments, the presence or absence of a birefringence signal from one or more optical view ports (as shown in tiles 708) may indicate whether or not one or more optical view ports in a catheter tip is in contact with tissue (e.g., a strong contact, an intermediate contact, a minimal contact, or no contact between the catheter and tissue). In some embodiments, the presence or absence of a birefringence signal from the one or more optical view ports may indicate whether or not there is a gap detected in between one or more lesions formed in an ablation line in tissue during and/or after ablation.

In some embodiments, the GUI 700 may include one or more graphs 710 showing ablation energy data (e.g., RF power), birefringence data, phase data, and predicted lesion depth data. In some embodiments, the GUI 700 may include one or more panels or indicators that show the occurrence of a stable contact between the catheter tip and tissue, loss in birefringence, status of the ablation energy (e.g., on/off), and predicted lesion depths. In some embodiments, the GUI 700 may include one or more buttons or text boxes that allow user selection and/or customization of parameters selected for ablation or for operating the catheter during ablation.

Figure 8:
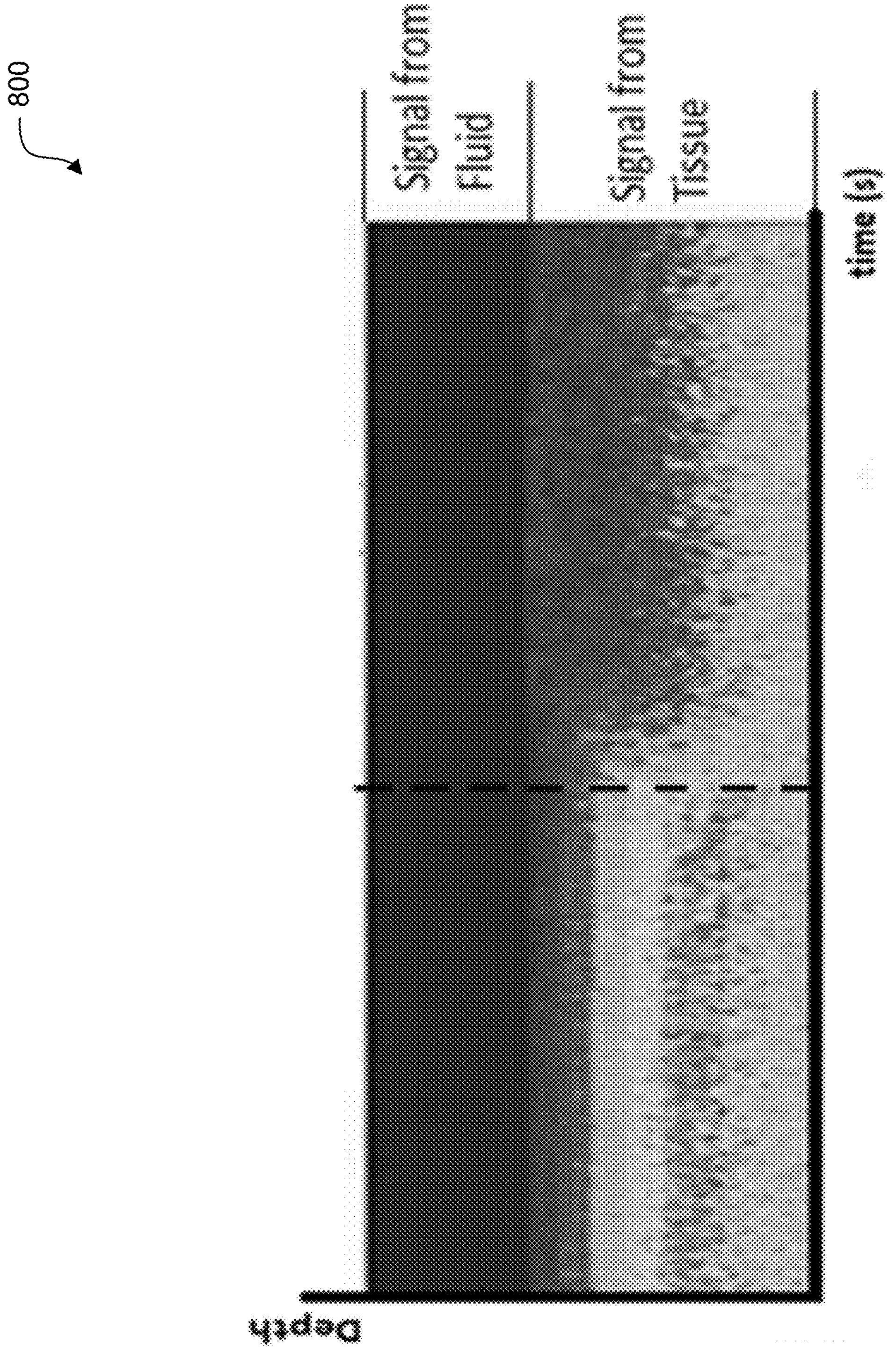
FIG. 8 illustrates an example diagram showing example results from optical measurements of tissue, according to embodiments of the present disclosure.

FIG. 8 illustrates an example diagram 800 showing example results from optical measurements of tissue, according to embodiments of the present disclosure. While FIG. 8 will be described with respect to birefringence, a person of skill in the art will recognize that other optical measurements may also be used to detect ablated tissue, in addition to or instead of birefringence, such as changes in polarization and/or spectral information (e.g., spectroscopic information or imaging information from tissue). In the example of FIG. 8, diagram 800 shows an example optical readout of birefringence of tissue from one or more optical signals measured by the optical view ports 508 in the catheter over a period of time. In some embodiments, the diagram 800 may represent an optical readout shown in one of the tiles 708 or in one of the graphs 710 in the GUI 700 of FIG. 7.

As shown in FIG. 8, diagram 800 shows that the tissue exhibits a loss in birefringence as the tissue undergoes ablation. In some embodiments, the birefringence signal of the tissue decreases upon cell death after a predetermined period of time (e.g., ablation time), as indicated by the vertical dashed line in the graph 800. In some embodiments, birefringence changes in tissue during or after ablation may be observed within a few seconds (e.g., less than 30 seconds) or within several minutes (e.g., up to 40 minutes) after delivery of PFA energy (e.g., pulse train) to the tissue. In some embodiments, the time for detection of changes in birefringence may depend on the strength (e.g., amplitude of pulse), type (monophasic, biphasic), frequency (e.g., frequency of pulse) and duration of the pulse train (e.g., the total time for all pulses to be delivered to the tissue). In some embodiments, if a change or reduction in birefringence is not detected within a predetermined time frame (such as in a range of about 1 second to about 1 hour), the clinician may re-ablate the tissue using a pulse train with the same or different characteristics.

Changes in birefringence may indicate whether or not there is a gap between one or more lesions formed in the portion of tissue. As the catheter is moved along an ablation line (in contact with the tissue), the signals returned from the tissue at a given location can be processed to indicate whether the tissue is sufficiently ablated at that location or not. For example, ablated tissue will not exhibit birefringence, while non-ablated or insufficiently ablated tissue will. In some embodiments, the presence of a gap between one or more lesions formed in an ablation line may be detected by identifying a birefringence signal in tissue through the optical view ports. In some embodiments, the absence of a gap between one or more lesions formed in an ablation line may be detected by identifying an absence of a birefringence signal in tissue through the optical view ports. For example, as the catheter is moved along an ablation line, a change in the birefringence signal from zero (or other low value) to a higher value may indicate that a gap exists in the ablation line where the tissue was not sufficiently ablated.

Exemplary Embodiments of Method of Operation

The catheters, consoles, and systems described herein may be used to perform optical analysis and gap detection of tissue. By utilizing the gap detection methods described herein, the catheter and optical systems disclosed herein (e.g., catheter system 300 and optical system 601) may allow evaluation of gaps in lesion formations in tissue in or near real-time, while providing greater precision for tissue locations that may need re-ablation.

Various methods and other embodiments of catheters and systems described thus far can be implemented, for example, using catheter 100 shown in FIG. 1, system 300 shown in FIG. 3 (including catheter 302 and console 310), catheter 400 shown in FIGS. 4, 5A, and 5B, optical system 601 shown in FIG. 6, and the embodiments shown in FIGS. 7-8.

Figure 9:
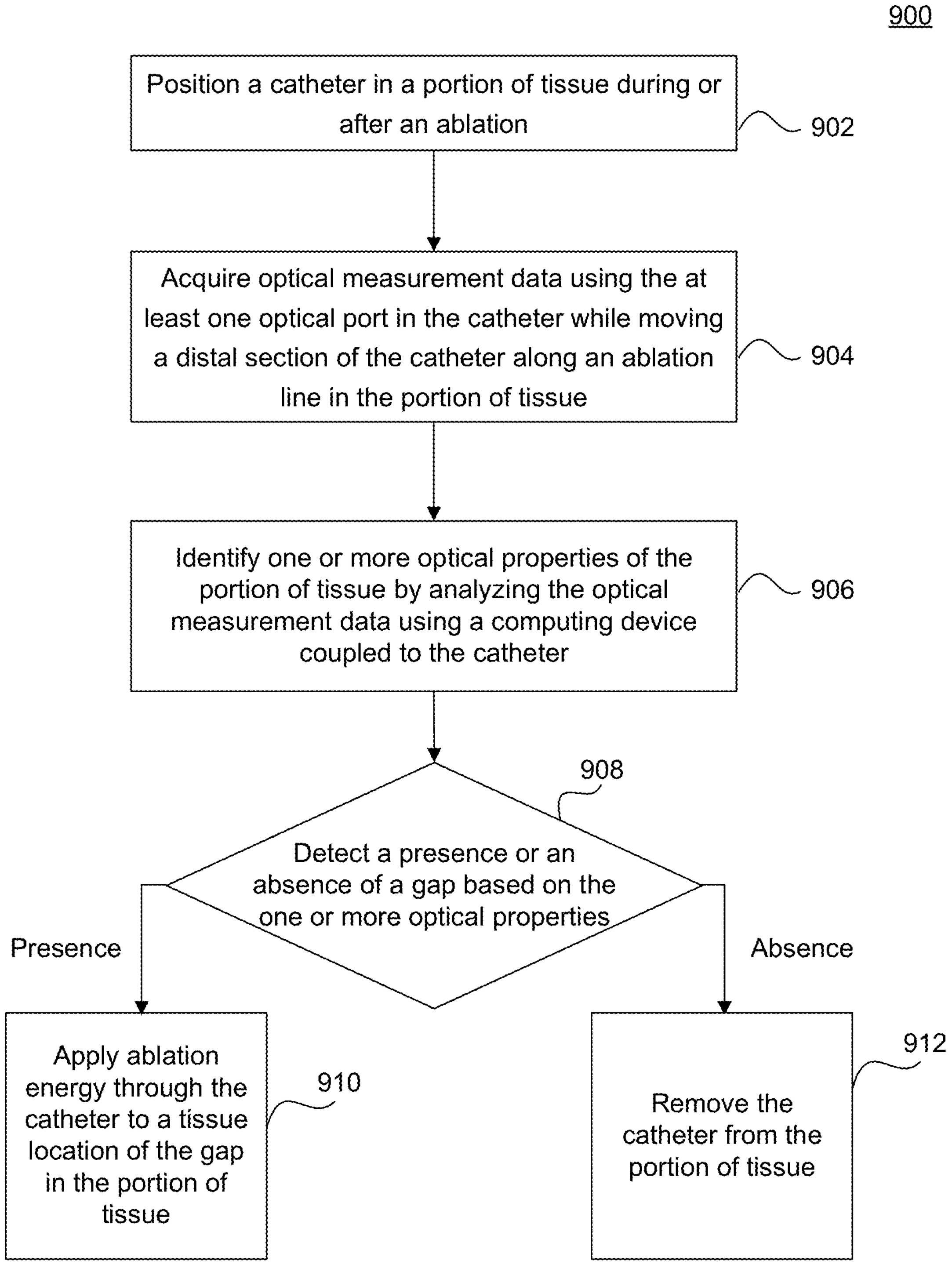
FIG. 9 illustrates an example method for detecting gaps between one or more lesions formed in tissue during ablation, according to embodiments of the present disclosure.

FIG. 9 illustrates an example method 900 for detecting gaps between one or more lesions formed in tissue during ablation, according to embodiments of the present disclosure. In some embodiments, method 900 may be performed by console 310 in FIG. 3, catheter 100, 302 or 400 in FIGS. 1, 4, 5A, and 5B, and/or optical system 601 in FIG. 6 as described herein.

At block 902, a catheter may be positioned in a portion of tissue during or after an ablation. In some embodiments, the catheter may include a proximal section, a distal section comprising a plurality of optical ports, and a shaft coupled between the proximal section and the distal section. In some embodiments, at least one optical port of the plurality of optical ports may be positioned to be in contact with the portion of tissue. In some embodiments, the energy applied by the catheter may be at least one of a pulsed electric field, radiofrequency (RF) energy, laser energy, cryogenic energy, or ultrasound energy.

At block 904, optical measurement data may be acquired from the portion of tissue using at least one optical port in the catheter while moving the distal section of the catheter along an ablation line in the portion of tissue. In some embodiments, the optical measurement data may include one or more optical coherence tomography (OCT) signals and/or optical coherence reflectometry (OCR) signals acquired from the portion of tissue. In some embodiments, the optical measurement data may be acquired by the optical system 410, and/or by the console 310. In some embodiments, the ablation line may include a plurality of ablation points in the portion of tissue where tissue has been ablated.

At block 906, one or more optical properties of the portion of tissue may be identified by analyzing the optical measurement data using a computing device coupled to the catheter. In some embodiments, the one or more optical properties include at least one of birefringence, polarization, and/or spectral information (e.g., spectroscopic information or imaging information from tissue).

At block 908, a presence or an absence of a gap may be detected based on the one or more optical properties. In some embodiments, the gap may be between one or more lesions formed in the ablation line in the portion of tissue. The gap may be a tissue region that has not formed a lesion in the portion of tissue. In some embodiments, the one or more optical properties of the portion of tissue may be birefringence. In some embodiments, a presence or absence of a gap between one or more lesions formed in the ablation line may be detected based on identifying whether or not there is birefringence in the portion of tissue. In an example, if birefringence is detected in the portion of tissue, then there is a gap between the one or more lesions in the portion of tissue. If there is no birefringence in the portion of tissue, then there are no gaps between the one or more lesions in the portion of tissue. In some embodiments, a user interface shown on display 325 may present a visualization in real-time of changes in birefringence during ablation or after ablation of tissue by catheter 302.

If a presence of a gap between one or more lesions is detected, then the method 900 in this example proceeds to block 910. At block 910, ablation energy may be applied through the catheter to a tissue location of the gap in the portion of tissue. In some embodiments, the ablation energy may be applied through a distal section of the catheter to the tissue location.

If an absence of a gap between one or more lesions is detected, then the method 900 in this example proceeds to block 912. At block 912, the catheter may be removed from the portion of tissue.

Exemplary Computing Embodiments

Figure 10:
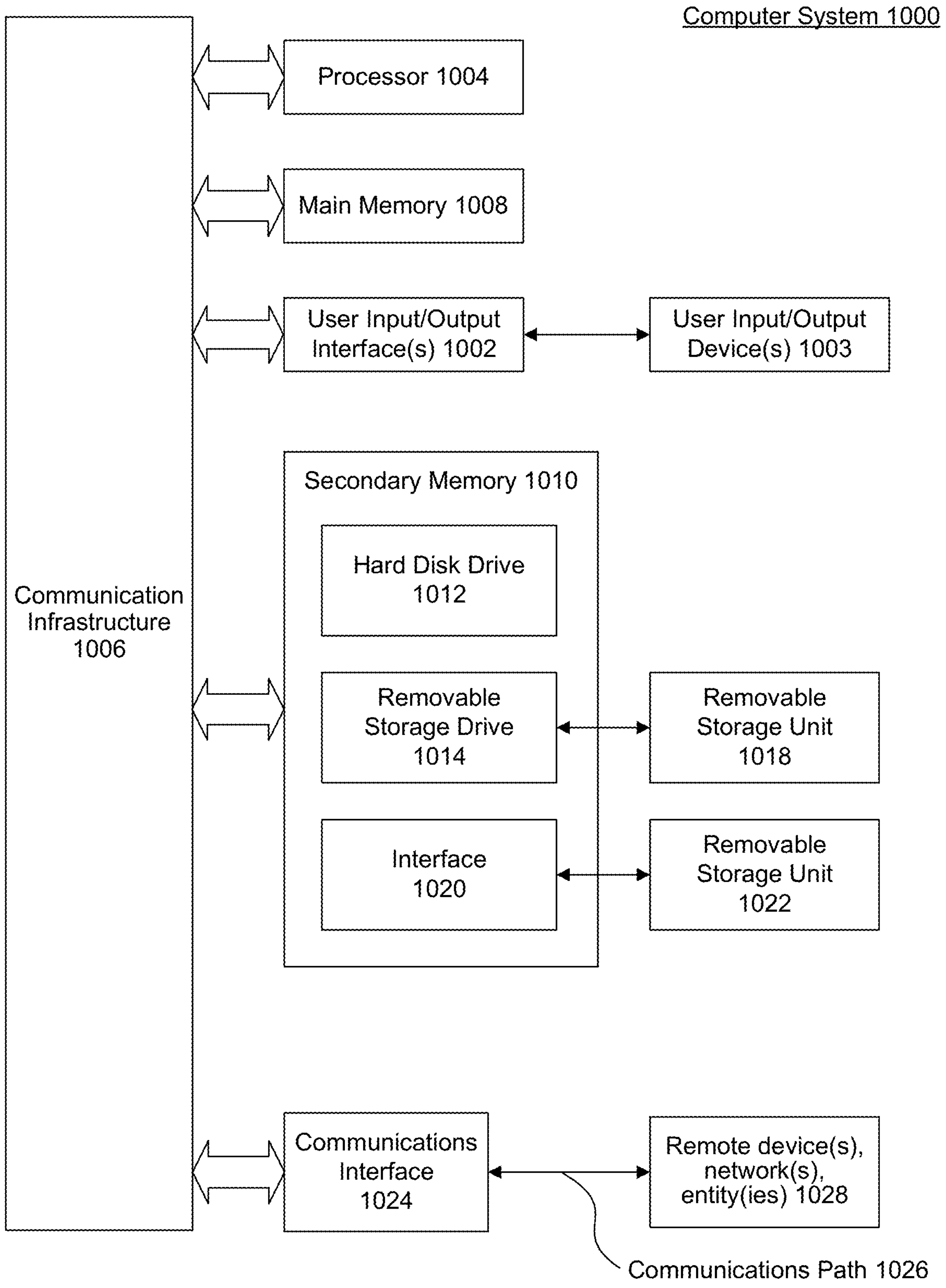
FIG. 10 illustrates a block diagram of example components of a computer system, according to embodiments of the present disclosure.

FIG. 10 is a block diagram of example components of computer system 1000. One or more computer systems 1000 may be used, for example, to implement any of the embodiments discussed herein, as well as combinations and sub-combinations thereof. In some embodiments, one or more computer systems 1000 may be used to implement the method 900 shown in FIG. 9, and/or console 310, signal generator 320, and display 325, as described herein. Computer system 1000 may include one or more processors (also called central processing units, or CPUs), such as a processor 1004. Processor 1004 may be connected to a communication infrastructure or bus 1006.

Computer system 1000 may also include user input/output interface(s) 1002, such as monitors, keyboards, pointing devices, etc., which may communicate with communication infrastructure 1006 through user input/output interface(s) 1003.

One or more of processors 1004 may be a graphics processing unit (GPU). In an embodiment, a GPU may be a processor that is a specialized electronic circuit designed to process mathematically intensive applications. The GPU may have a parallel structure that is efficient for parallel processing of large blocks of data, such as mathematically intensive data common to computer graphics applications, images, videos, etc.

Computer system 1000 may also include a main or primary memory 1008, such as random access memory (RAM). Main memory 1008 may include one or more levels of cache. Main memory 1008 may have stored therein control logic (i.e., computer software) and/or data. In some embodiments, main memory 1008 may include optical logic configured to perform analysis of optical measurements obtained from tissue by a catheter and detect gaps lesion.

Computer system 1000 may also include one or more secondary storage devices or memory 1010. Secondary memory 1010 may include, for example, a hard disk drive 1012 and/or a removable storage drive 1014.

Removable storage drive 1014 may interact with a removable storage unit 1018. Removable storage unit 1018 may include a computer usable or readable storage device having stored thereon computer software (control logic) and/or data. Removable storage unit 1018 may be a program cartridge and cartridge interface (such as that found in video game devices), a removable memory chip (such as an EPROM or PROM) and associated socket, a memory stick and USB port, a memory card and associated memory card slot, and/or any other removable storage unit and associated interface. Removable storage drive 1014 may read from and/or write to removable storage unit 1018.

Secondary memory 1010 may include other means, devices, components, instrumentalities or other approaches for allowing computer programs and/or other instructions and/or data to be accessed by computer system 1000. Such means, devices, components, instrumentalities or other approaches may include, for example, a removable storage unit 1022 and an interface 1020. Examples of the removable storage unit 1022 and the interface 1020 may include a program cartridge and cartridge interface (such as that found in video game devices), a removable memory chip (such as an EPROM or PROM) and associated socket, a memory stick and USB port, a memory card and associated memory card slot, and/or any other removable storage unit and associated interface.

Computer system 1000 may further include a communication or network interface 1024. Communication interface 1024 may enable computer system 1000 to communicate and interact with any combination of external devices, external networks, external entities, etc. (individually and collectively referenced by reference number 10210). For example, communication interface 1024 may allow computer system 1000 to communicate with external or remote devices 1028 over communications path 1026, which may be wired and/or wireless (or a combination thereof), and which may include any combination of LANs, WANs, the Internet, etc. Control logic and/or data may be transmitted to and from computer system 1000 via communication path 1026. In some embodiments, computer system 1000 may be coupled to a catheter via a connector and optical and electrical connections at communication interface 1024, including optical fibers and electrical wiring, pins, and/or components.

Computer system 1000 may also be any of a personal digital assistant (PDA), desktop workstation, laptop or notebook computer, netbook, tablet, smartphone, smartwatch or other wearables, appliance, part of the Internet-of-Things, and/or embedded system, to name a few non-limiting examples, or any combination thereof.

Computer system 1000 may be a client or server, accessing or hosting any applications and/or data through any delivery paradigm, including but not limited to remote or distributed cloud computing solutions; local or on-premises software ("on-premise" cloud-based solutions); "as a service" models (e.g., content as a service (CaaS), digital content as a service (DCaaS), software as a service (SaaS), managed software as a service (MSaaS), platform as a service (PaaS), desktop as a service (DaaS), framework as a service (FaaS), backend as a service (BaaS), mobile backend as a service (MBaaS), infrastructure as a service (IaaS), etc.); and/or a hybrid model including any combination of the foregoing examples or other services or delivery paradigms.

Any applicable data structures, file formats, and schemas in computer system 1000 may be derived from standards including but not limited to JavaScript Object Notation (JSON), Extensible Markup Language (XML), Yet Another Markup Language (YAML), Extensible Hypertext Markup Language (XHTML), Wireless Markup Language (WML), MessagePack, XML User Interface Language (XUL), or any other functionally similar representations alone or in combination. Alternatively, proprietary data structures, formats or schemas may be used, either exclusively or in combination with known or open standards.

In some embodiments, a tangible, non-transitory apparatus or article of manufacture comprising a tangible, non-transitory computer useable or readable medium having control logic (software) stored thereon may also be referred to herein as a computer program product or program storage device. This includes, but is not limited to, computer system 1000, main memory 1008, secondary memory 1010, and removable storage units 1018 and 1022, as well as tangible articles of manufacture embodying any combination of the foregoing. Such control logic, when executed by one or more data processing devices (such as computer system 1000), may cause such data processing devices to operate as described herein.

It is to be appreciated that the Detailed Description section, and not the Summary and Abstract sections, is intended to be used to interpret the claims. The Summary and Abstract sections may set forth one or more but not all exemplary embodiments of the present disclosure as contemplated by the inventor(s), and thus, are not intended to limit the present disclosure and the appended claims in any way.

Embodiments of the present disclosure have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments, but should be defined only in accordance with the following claims and their equivalents.

What is claimed is:

1. A computer-implemented method comprising:

acquiring, by a computing device coupled to a catheter, optical measurement data from the catheter when the catheter is positioned in a portion of tissue during or after an ablation, the catheter comprising a proximal section, a distal section comprising a plurality of optical ports, and a shaft coupled between the proximal section and the distal section, wherein at least one optical port of the plurality of optical ports is in contact with the portion of tissue, and wherein the acquiring comprises using the at least one optical port of the plurality of optical ports and occurs while the distal section of the catheter is moved along an ablation line in the portion of tissue;

identifying, by the computing device, one or more optical properties of the portion of tissue by analyzing the optical measurement data;

detecting, by the computing device, a presence or an absence of a gap between one or more lesions formed in the ablation line in the portion of tissue, wherein detecting the presence or the absence of the gap between the one or more lesions formed in the ablation line in the portion of the tissue comprises:

determining that the gap is present between the one or more lesions formed in the ablation line based on identifying birefringence in the portion of tissue, or determining that the gap is absent between the one or more lesions formed in the ablation line based on identifying an absence of birefringence in the portion of tissue; and providing, by the computing device, an indication of the presence or the absence of the gap to a user.

2. The method of claim 1, wherein the ablation line comprises a plurality of ablation points in the portion of tissue where tissue has been ablated.

3. The method of claim 1, wherein the gap comprises a tissue region that has not formed a lesion of the one or more lesions in the portion of tissue.

4. The method of claim 1, wherein the optical measurement data comprises an optical coherence tomography (OCT) signal or an optical coherence reflectometry (OCR) signal acquired from the portion of tissue.

5. The method of claim 1, wherein the one or more optical properties comprise at least one of birefringence, polarization, or spectral information.

6. The method of claim 1, further comprising:

in response to detecting the presence of the gap, applying ablation energy through the distal section of the catheter to a tissue location of the gap in the portion of tissue.

7. The method of claim 6, wherein the ablation energy applied by the catheter comprises at least one of a pulsed electric field, radiofrequency (RF) energy, laser energy, or cryogenic energy.

8. A system comprising:

a catheter comprising a proximal section, a distal section, and a shaft coupled between the proximal section and the distal section;

a plurality of optical fibers located within the catheter; and a computing device coupled to the plurality of optical fibers, the computing device comprising a memory and a processor configured to:

receive, from at least one optical fiber in the plurality of optical fibers, optical measurement data of a portion of tissue during or after an ablation;

identify one or more optical properties of the portion of tissue by analyzing the optical measurement data;

detect a presence or an absence of a gap between one or more lesions formed in an ablation line in the portion of tissue, wherein, to detect the presence or the absence of the gap between the one or more lesions, the processor is configured to:

determine that the gap is present between the one or more lesions formed in the ablation line based on identifying birefringence in the portion of tissue, or determine that the gap is absent between the one or more lesions formed in the ablation line based on identifying an absence of birefringence in the portion of tissue; and provide an indication of the presence or the absence of the gap to a user.

9. The system of claim 8, wherein the gap comprises a tissue region that has not formed a lesion of the one or more lesions in the portion of tissue.

10. The system of claim 8, wherein the optical measurement data comprises an optical coherence tomography (OCT) signal or an optical coherence reflectometry (OCR) signal acquired from the portion of tissue.

11. The system of claim 8, wherein the one or more optical properties comprise at least one of birefringence, polarization, or spectral information.

12. The system of claim 8, wherein the processor is configured to receive the optical measurement data while the catheter is moved along the ablation line in the portion of tissue, wherein the ablation line comprises a plurality of ablation points in the portion of tissue where tissue has been ablated.

13. The system of claim 8, wherein ablation energy applied by the catheter comprises at least one of a pulsed electric field, radiofrequency (RF) energy, laser energy, or cryogenic energy.

14. A computing device comprising:

a memory; and a processor coupled to the memory, where the processor is configured to:

receive, from a catheter, optical measurement data of a portion of tissue while the catheter is moved along an ablation line in the portion of tissue;

identify one or more optical properties of the portion of tissue by analyzing the optical measurement data;

detect a presence or an absence of a gap between one or more lesions formed in an ablation line in the portion of tissue, wherein, to detect the presence or the absence of the gap between the one or more lesions, the processor is configured to:

determine that the gap is present between the one or more lesions formed in the ablation line based on identifying birefringence in the portion of tissue, or determine that the gap is absent between the one or more lesions formed in the ablation line based on identifying an absence of birefringence in the portion of tissue; and provide an indication of the presence or the absence of the gap to a user.

15. The computing device of claim 14, wherein the optical measurement data comprises an optical coherence tomography (OCT) signal or an optical coherence reflectometry (OCR) signal acquired from the portion of tissue, and wherein the one or more optical properties comprise at least one of birefringence, polarization, or spectral information.

* * * * *